United States Patent
Shimazu et al.

(10) Patent No.: US 10,687,714 B2
(45) Date of Patent: Jun. 23, 2020

(54) VASCULAR ELASTICITY RATE EVALUATION APPARATUS

(71) Applicant: SANYOSEIKO CO., LTD., Ootsuki-shi, Yamanashi (JP)

(72) Inventors: Hideaki Shimazu, Tokyo (JP); Futoshi Shirakawa, Ootsuki (JP); Yasuyuki Yaguchi, Okaya (JP)

(73) Assignee: SANYOSEIKO CO., LTD., Yamanashi (JP)

( * ) Notice: Subject to any disclaimer, the term of this patent is extended or adjusted under 35 U.S.C. 154(b) by 0 days.

(21) Appl. No.: 15/310,617

(22) PCT Filed: Mar. 29, 2016

(86) PCT No.: PCT/JP2016/060078
§ 371 (c)(1),
(2) Date: Nov. 11, 2016

(87) PCT Pub. No.: WO2017/098739
PCT Pub. Date: Jun. 15, 2017

(65) Prior Publication Data
US 2018/0263505 A1  Sep. 20, 2018

(30) Foreign Application Priority Data

Dec. 7, 2015 (JP) ................. 2015-238727

(51) Int. Cl.
*A61B 5/02* (2006.01)
*A61B 5/021* (2006.01)
(Continued)

(52) U.S. Cl.
CPC .......... *A61B 5/02007* (2013.01); *A61B 5/022* (2013.01); *A61B 5/02116* (2013.01);
(Continued)

(58) Field of Classification Search
CPC . A61B 5/022; A61B 5/02007; A61B 5/02116; A61B 5/7242; A61B 5/0225; A61B 5/02233; A61B 5/02108
See application file for complete search history.

(56) References Cited

U.S. PATENT DOCUMENTS

| 5,680,867 A | 10/1997 | Shimazu et al. |
| 5,961,467 A | 10/1999 | Shimazu et al. |

(Continued)

FOREIGN PATENT DOCUMENTS

| CN | 1226812 A | 8/1999 |
| CN | 101156771 A | 4/2008 |

(Continued)

OTHER PUBLICATIONS

Extended European Search Report corresponding to Application No. 16791291.4-1115/3199101 PCT/JP2016060078; dated Jun. 27, 2018.

(Continued)

*Primary Examiner* — Christian Jang
(74) *Attorney, Agent, or Firm* — Cantor Colburn LLP

(57) ABSTRACT

To perform measurement of a vascular elasticity rate with high accuracy in a short time. A vascular elasticity rate evaluation apparatus of the present invention includes: a pressure detection unit that detects a pulse wave with an external pressure being applied to a blood vessel; and a control unit that forms a pulse wave amplitude indicating dependent characteristics due to elasticity of the blood vessel from a detection value of the pressure detection unit, calculates a plus area in an elevation process of the pulse wave amplitude and a minus area in a descent process thereof, and calculates the vascular elasticity rate using values thereof.

3 Claims, 6 Drawing Sheets

(51) Int. Cl.
*A61B 5/022* (2006.01)
*A61B 5/00* (2006.01)
*A61B 5/0225* (2006.01)

(52) U.S. Cl.
CPC .......... *A61B 5/7278* (2013.01); *A61B 5/0225* (2013.01); *A61B 5/02108* (2013.01); *A61B 5/02233* (2013.01); *A61B 5/7242* (2013.01)

(56) References Cited

U.S. PATENT DOCUMENTS

| | | | |
|---|---|---|---|
| 6,186,954 B1 * | 2/2001 | Narimatsu | A61B 5/022 600/485 |
| 6,210,340 B1 | 4/2001 | Amano et al. | |
| 2005/0256412 A1 | 11/2005 | Shimazu et al. | |
| 2013/0023777 A1 | 1/2013 | Tokko et al. | |
| 2014/0194756 A1 | 7/2014 | Sazuka | |
| 2015/0250394 A1 | 9/2015 | Ono et al. | |
| 2016/0051151 A1 | 2/2016 | Saito et al. | |

FOREIGN PATENT DOCUMENTS

| | | |
|---|---|---|
| CN | 101791216 A | 8/2010 |
| CN | 102811660 A | 12/2012 |
| CN | 104887195 A | 9/2015 |
| EP | 2606818 A1 | 6/2013 |
| EP | 2918224 A1 | 9/2015 |
| JP | 2000116608 A | 4/2000 |
| JP | 3470121 B2 | 11/2003 |
| JP | 3626171 B1 | 3/2005 |
| JP | 2007313145 A | 12/2007 |
| JP | 2008061824 A | 3/2008 |
| JP | 2012239799 A | 12/2012 |
| JP | 2013144125 A | 7/2013 |
| JP | 2014188035 A | 10/2014 |

OTHER PUBLICATIONS

KIPO Notification of Reason for Refusal for corresponding KR Application No. 10-2016-7024613; dated Apr. 9, 2018.
SIPO First Office Action corresponding to Application No. 201680000882.9; dated Jun. 28, 2019.

* cited by examiner

VASCULAR ELASTICITY RATE EVALUATION APPARATUS

This is the U.S. national stage of application No. PCT/JP2016/060078, filed on Mar. 29, 2016. Priority under 35 U.S.C. $119(a) and 35 U.S.C. $365(b) is claimed from Japanese Application No. 2015-238727, filed Dec. 7, 2015, the disclosure of which is also incorporated herein by reference.

TECHNICAL FIELD

The present invention relates to a vascular elasticity rate evaluation apparatus.

BACKGROUND ART

The present inventors have proposed an electronic blood pressure measuring apparatus that catches and analyzes a pulse wave amplitude pattern from an oscillation occurring in a cuff due to pulsation of the artery under the cuff by measurement of the blood pressure by the oscillometric method (refer to PTL 1). The present inventors further have proposed a hemodynamics evaluating apparatus that derives a hemodynamics index relating to the kinetic property of a blood vessel and/or the pumping property of a heart from the above-described pulse wave amplitude pattern (refer to PTL 2). Further, PTL 3 discloses an apparatus that inspects the blood pressure/pulse wave by a plurality of cuffs wound around a plurality of portions including the upper arm and the lower leg of a subject.

The hemodynamics evaluating apparatus in PTL 2 derives the hemodynamics index relating to the kinetic property of a blood vessel and/or the pumping property of a heart on the basis of the pulse wave amplitude pattern obtained in a process of blood pressure measurement one time. In this event, the hemodynamics evaluating apparatus in PTL 2 acquires the pulse wave amplitude pattern one time in a process of pressurizing the cuff wound around the measurement portion of the subject and then pressurizing the cuff. This process generally requires several tens of seconds. Note that the above-described kinetic property of a blood vessel is, for example, an elasticity rate of the blood vessel.

CITATION LIST

Patent Literature

{PTL 1} JP 3470121
{PTL 2} JP 3626171
{PTL 3} JP 5752162

SUMMARY OF INVENTION

Technical Problem

To increase the accuracy of the measurement in the hemodynamics evaluating apparatus in PTL 2, it is necessary to acquire the pulse wave amplitude pattern a plurality of times. Acquisition of the pulse wave amplitude pattern a plurality of times requires a time period of several minutes. Such measurement a plurality of times puts stress on the subject. Besides, when the measurement is performed a plurality of times on many subjects, waiting time becomes longer for subjects whose turns are later.

Besides, the blood pressure/pulse wave inspection apparatus in PTL 3 inspects the blood pressure/pulse wave by the plurality of cuffs wound around the plurality of portions including the upper arm and the lower leg of the subject, and therefore cannot specify local problems of the blood vessel of the subject.

The present invention has been made under such a background, and its object is to provide a vascular elasticity rate evaluation apparatus capable of performing measurement with high accuracy in a short time, and capable of measuring a vascular elasticity rate at a specific portion of a subject.

Solution to Problem

The present invention is a vascular elasticity rate evaluation apparatus including: a pulse wave detection means for detecting a pulse wave with an external pressure being applied to a blood vessel; a means for forming a pulse wave amplitude indicating dependent characteristics due to elasticity of the blood vessel from a detection value of the pulse wave detection means; and an elasticity rate deriving means for calculating a plus area in an elevation process of the pulse wave amplitude and a minus area in a descent process thereof, and deriving a vascular elasticity rate using values thereof.

Alternatively, the present invention is a vascular elasticity rate evaluation apparatus including: a pulse wave detection means for detecting a pulse wave with an external pressure being applied to a blood vessel; a means for forming a pulse wave amplitude indicating dependent characteristics due to elasticity of the blood vessel from a detection value of the pulse wave detection means; and an elasticity rate deriving means for calculating a volume change rate of the blood vessel in an elevation process of the pulse wave amplitude and a volume change rate of the blood vessel in a descent process thereof, and deriving a vascular elasticity rate using values thereof.

In this case, the elasticity rate deriving means can replace a value derived from the volume change rate of the blood vessel being a rate of the volume change of the blood vessel in a predetermined time with a length of one side of a rectangle, can replace a value derived from the predetermined time with a length of another side adjacent to the one side of the rectangle, can set an area of the rectangle obtained by multiplying the length of the one side and the length of the another side as a volume change rate area, and can calculate a plus volume change rate area in the elevation process of the pulse wave amplitude and a minus volume change rate area in the descent process thereof, and can calculate the vascular elasticity rate using values thereof. Note that a square is included as one form of the rectangle as a matter of course.

In the above-described vascular elasticity rate evaluation apparatus, the elasticity rate deriving means can derive the vascular elasticity rate in a limited range from a minimum blood pressure to a maximum blood pressure of the pulse wave amplitude.

In the above-described vascular elasticity rate evaluation apparatus, the elasticity rate deriving means can use a logarithm when deriving the vascular elasticity rate.

In the above-described vascular elasticity rate evaluation apparatus, the elasticity rate deriving means can set a reciprocal of the derived vascular elasticity rate as an index of the vascular elasticity rate.

A vascular elasticity rate evaluation apparatus of the present invention includes: a pulse wave detection means for detecting a pulse wave with an external pressure being applied to a blood vessel; a means for forming a pulse wave amplitude indicating dependent characteristics due to elasticity of the blood vessel from a detection value of the pulse wave detection means; and an elasticity rate deriving means for deriving a vascular elasticity rate using measured values in processes for an elevation process and a descent process of the pulse wave amplitude.

The above-described vascular elasticity rate evaluation apparatus can further include a means for individually displaying vascular elasticity rates measured at a plurality of portions of a subject.

The above-described vascular elasticity rate evaluation apparatus can further include a plurality of the pulse wave detection means, wherein the elasticity rate deriving means can sequentially or simultaneously measure the vascular elasticity rates at a plurality of portions of a subject.

Advantageous Effects of Invention

According to the present invention, it is possible to perform measurement of avascular elasticity rate with high accuracy in a short time, and to measure the vascular elasticity rate at a specific portion of a subject.

DESCRIPTION OF EMBODIMENTS

Figure 1:
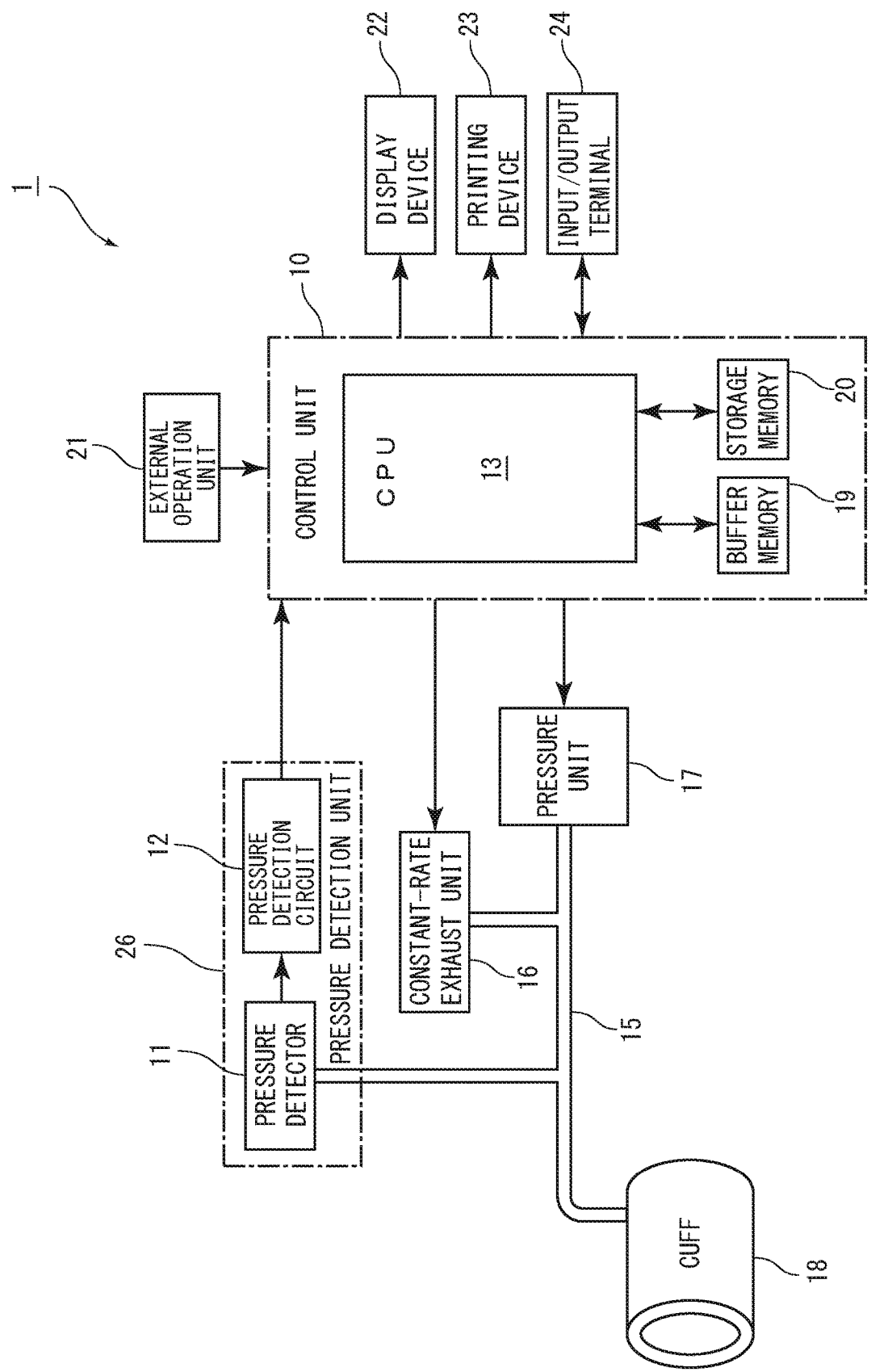
FIG. 1 is a block diagram of a vascular elasticity rate evaluation apparatus according to an embodiment of the present invention.

A vascular elasticity rate evaluation apparatus 1 according to an embodiment of the present invention will be described referring to the drawings. FIG. 1 is a block diagram of the vascular elasticity rate evaluation apparatus 1 according to the embodiment of the present invention. The vascular elasticity rate evaluation apparatus 1 includes: a cuff 18 for compressing a blood vessel (artery) of a living body, namely, an inflatable arm belt which can be inflated; a pressure detector 11 for detecting a cuff pressure, composed of a diaphragm gage, a strain sensor and so on; a constant-rate exhaust unit 16 for exhausting air in the cuff 18, composed of a flow control valve, a pressure reducing valve and so on; and a pressure unit 17 for increasing the pressure in the cuff 18, composed of a pressure pump and so on, which are connected to one another via a pipe 15 composed of a flexible tube and so on.

The pressure detector 11 is to detect the pressure in the cuff 18, namely, the cuff pressure, and outputs a detection signal representing the cuff pressure to a pressure detection circuit 12. The pressure detection circuit 12 converts (for example, A/D (analog-digital) converts) the detection signal of the pressure detector 11, and outputs the converted detection signal to a control unit 10 composed of an MPU (microprocessor unit) or the like.

Here, the pressure detector 11 and the pressure detection circuit 12 constitute a pressure detection unit 26, and the pressure detection unit 26 becomes a part of a pulse wave detection means. The pulse wave detection means is composed of the cuff 18 and the pressure detection unit 26.

Further, the later-described control unit 10 operates as a means for forming a pulse wave amplitude indicating dependent characteristics due to the elasticity of the blood vessel from a detection value of the pulse wave detection means, by part of various operating programs executed by the control unit 10.

The control unit 10 has a CPU (central processing unit) 13, a buffer memory 19 composed of a RAM (random access memory) or the like, and a storage memory 20 composed of a ROM(read-only memory) or the like, and additionally includes an internal bus, an input/output circuit and so on as necessary. The buffer memory 19 temporarily records processing results of the operating programs executed by the CPU 13. Further, in the storage memory 20, the above-described operating programs, various set values, reference values and so on are recorded.

To the control unit 10, an external operation unit 21 having external operation members such as an operation switch, a display device 22 for visually displaying the processing results, a printing device 23 for recording the processing results on a medium such as paper, and an input/output terminal 24 for outputting the processing results and inputting data from the outside are connected.

Note that the control unit 10 does not have to be composed of the MPU as described above, but may be composed of a simple arithmetic circuit. Besides, a detection system including the cuff 18 and a control system mainly including the control unit 10 are integrally constituted in this embodiment, but the detection system and the control system may be separately constituted. For example, a detection device constituting the detection system and a control device composed of a personal computer or the like may be used. Besides, the operating programs are executed to perform detection processing and analysis processing on detection results in this embodiment, but a detection processing program for executing the detection processing and an analysis processing program for performing analysis processing on the detection results may be separately prepared.

Figure 2:
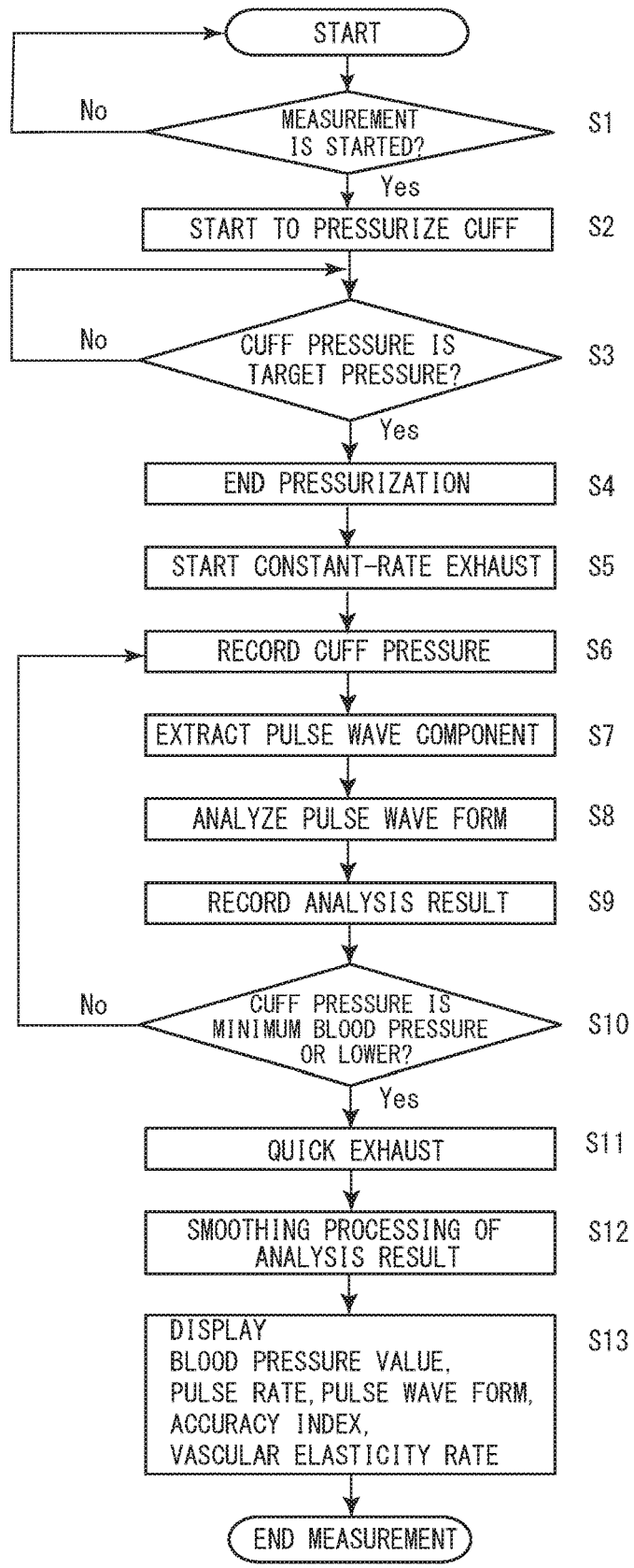
FIG. 2 is a schematic flowchart schematically illustrating an operation procedure of operating programs in this embodiment executed by a control unit.

FIG. 2 is a schematic flowchart schematically illustrating an operation procedure of the operating programs in this embodiment executed by the control unit 10 as an elasticity rate deriving means. In the case of using the vascular elasticity rate evaluation apparatus 1 in this embodiment, first, the cuff 18 is wound around a portion where the artery of a subject can be compressed. Here, the place around which the cuff 18 is wound may be any place where the artery can be compressed and the blood pressure can be measured, such as an arm, an ankle, a wrist or the like.

Thereafter, upon start of operation at the external operation unit 21, measurement is started (S1), and the control unit 10 supplies a drive signal to the pressure unit 17 to pressurize the cuff 18 (S2). Note that in this pressurization process, preferably, the constant-rate exhaust unit 16 is closed and the exhaust is stopped. In this event, the cuff pressure is detected by the pressure detection unit 26, and when the cuff pressure reaches a target pressure (S3), the control unit 10 ends the pressurization by the pressure unit 17 (S4). The target pressure is set at a pressure sufficiently higher than the maximum blood pressure of the subject, for example, about 210 mmHg.

Then, when the above-described pressurization process ends, exhaust by the constant-rate exhaust unit 16 is started (S5), and the cuff pressure is continuously detected by the pressure detection unit 26 and recorded in the buffer memory 19 of the control unit 10 (S6). At this step, the pressure detection circuit 12 sequentially samples the detection value from the pressure detector 11 at a time interval of a predetermined sampling period, for example, 50 msec, and the cuff pressure corresponding to the detection value is recorded in the buffer memory 19 of the control unit 10.

Further, a pulse wave component is extracted based on the cuff pressure detected at this time (S7), and an extracted pulse wave form is analyzed using a later-described calculation expression (S8). The analysis result is recorded in the buffer memory 19 (S9). More specifically, the control unit 10 obtains a difference value in supplied cuff pressure data, removes a component corresponding to a rate of decrease in cuff pressure from the difference data sequence, and then integrates only positive difference data for each pulse wave to derive a pulse wave amplitude. Thus, the form of the pulse wave is detected from the amplitude of the pulse wave.

Then, the form of the pulse wave is analyzed by a later-described calculation expression, and its analysis result is recorded in the buffer memory 19 together with the value of the cuff pressure and its generation time. In this analysis processing, decision of the maximum blood pressure value, decision of the average blood pressure value, decision of the minimum blood pressure value, decision of the pulse rate and so on are performed in addition to the analysis of the pulse wave form.

The processing at Steps S6 to S10 is repeatedly performed until the cuff pressure reaches the minimum blood pressure or lower at Step S10. Generally, about 7 pulse waves are often observed within a time when the processing at Steps S6 to S10 is executed. In other words, during the time when the processing at Steps S6 to S10 is repeatedly executed, the analysis of the pulse wave form is performed about seven times.

When the cuff pressure lowers to the minimum blood pressure or lower (S10), the measurement of the cuff pressure ends, the constant-rate exhaust unit 16 is opened, and thereby quick exhaust is performed (S11).

When the above measurement ends, the control unit 10 performs smoothing processing on the analysis result of the obtained pulse wave form (S12). In this processing, whether the analysis result of the pulse wave form is a normal analysis result or not is determined by comparing the previous analysis result of the pulse wave form, the current analysis result of the pulse wave form, and the next analysis result of the pulse wave form. When there is an abnormal analysis result as compared with the previous and subsequent data, this analysis result is removed and replaced with an average value of the previous and subsequent data or the like. Further, by taking a moving average of the analysis result data sequence, the smoothing processing of the analysis result data sequence is performed. This removes abnormal data from the data sequence of the analysis result of the pulse wave form, and decreases a fine fluctuation component due to noise.

Note that a pulse wave detection method by the pulse wave detection means according to the embodiment of the present invention only needs to be the one that can obtain the above-described pulse wave form as a result, and therefore is not limited to a method of detecting the pulse wave while gradually decreasing the cuff pressure as described above, but a method of detecting the pulse wave while gradually increasing the cuff pressure or a method of detecting the pulse wave while arbitrarily changing the cuff pressure may be used to measure the data. In any case, the pulse wave form and the external pressure (or a pressure difference between the inside and the outside of the blood vessel) when the pulse wave form is obtained only need to be measured in a predetermined range including both sides centered on the vicinity of the average blood pressure of the subject.

Lastly, the blood pressure values, pulse rate, pulse wave form, accuracy index (described later in detail), vascular elasticity rate (described later in detail) and so on obtained by the above-described analysis processing are displayed on the display device 22, printed by the printing device 23, or outputted as data by the input/output terminal 24 (S13).

Note that, in the flowchart in FIG. 2, analysis of the pulse wave form and recording of the analysis result are performed for each pulse at Steps S8, S9. In contrast to this, as another method, only the pulse wave component for each pulse extracted at Step S7 may be recorded, and the recorded pulse wave component may be read during Step S10 to Step S12, namely, after the measurement of the blood pressure is completely finished, and then the processing at Steps S8, S9 may be performed.

Figure 3:
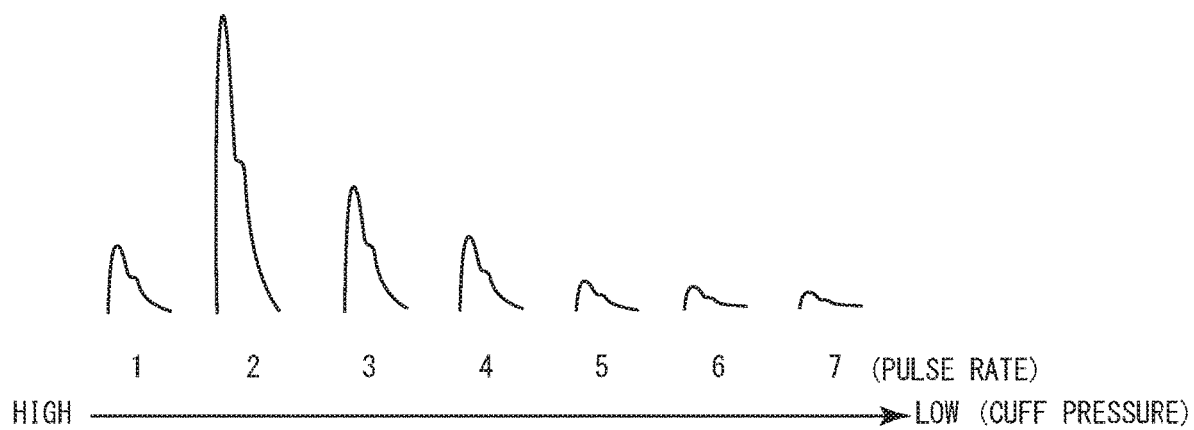
FIG. 3 is a chart illustrating a state of pulse waves accompanying a process of blood pressure measurement.

Next, a specific method of the above-described analysis of the pulse wave form (S8) will be described. FIG. 3 is a chart illustrating the state of the pulse waves accompanying the process of blood pressure measurement. As illustrated in FIG. 3, when the pressure of the cuff 18 shifts from the higher side to the lower side, about seven pulsations are generally made. With the cuff pressure at a value slightly higher than the maximum blood pressure (the pressure difference between the inside and the outside of the blood vessel is negative at all times), the blood vessel is squashed to cause no volume change of the blood vessel. Therefore, an oscillation phenomenon of the pressure is not transmitted to the cuff 18. In this event, the volume change appears like "1" in FIG. 3.

When the cuff pressure is gradually reduced from the value of the maximum blood pressure or higher, the amplitude of the volume change of the blood vessel changes from "1" to "7" in FIG. 3 with the depressurization of the cuff 18. In this process, the blood vessel expands with the depressurization of the cuff 18, and the blood vessel volume change amount corresponding to the pulse pressure also gradually increases. In the state where the cuff pressure is coincident with the average blood pressure of the subject, an average pressure difference between the inside and the outside of the blood vessel becomes substantially zero, and the volume change corresponding to the change in pressure (pulse pressure) becomes largest like "2" in FIG. 3. This can be used to determine the average blood pressure from the cuff pressure corresponding to a point where the pulse wave amplitude becomes maximum in the pressure reduction process of the cuff pressure. The control unit 10 as the elasticity rate deriving means derives the vascular elasticity rate (described later in detail) on the basis of the degree of change in pulse wave amplitude between an elevation process and a descent process in a limited range from the minimum blood pressure to the maximum blood pressure.

In the above-described analysis of the pulse wave form, it is only necessary to be able to detect the form of each pulse wave regardless of the magnitude of the cuff pressure.

Hence, the pulse wave form is detected by detecting the pulse wave amplitude when the cuff pressure is regarded as constant in each of the pulse waves "1" to "7". An example of the pulse wave form detected as described above is illustrated in FIG. 4. The amplitude of the pulse wave illustrated in FIG. 4 falls within a range of the minimum blood pressure to the maximum blood pressure. The form of the pulse wave is generally, as illustrated in FIG. 4, divided into a pre-ejection wave 30, an anacrotic limb 31, a peak 32, a tidal wave 33, a dicrotic notch 34, and a dicrotic wave 35.

Figure 4:
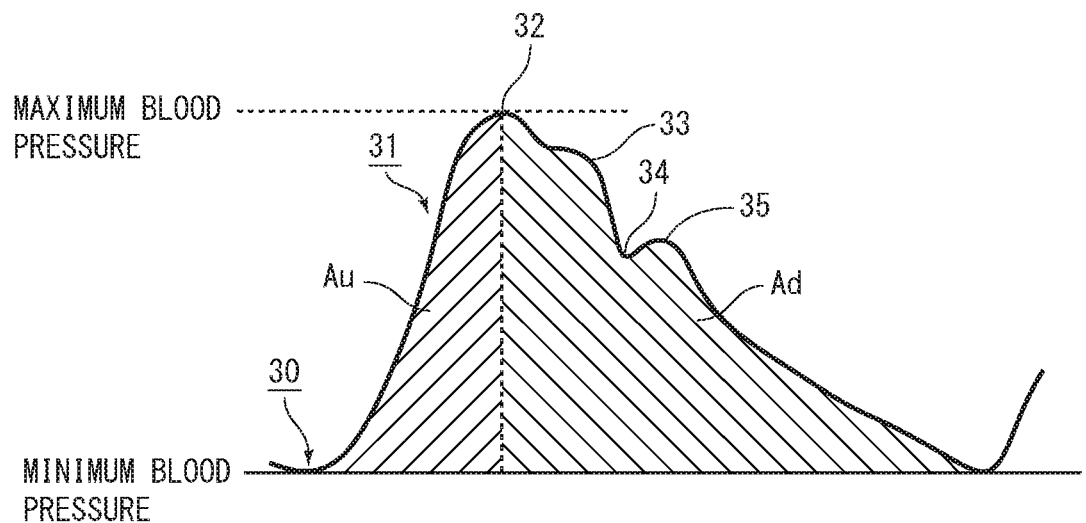
FIG. 4 is a chart illustrating a state of one of the pulse waves illustrated in FIG. 3 taken out, illustrating a state where the vascular elasticity rate is large.

The pre-ejection wave 30 is composed of some small waves observed before rise of the arterial pulse wave elevation and exists immediately before the anacrotic limb 31, and is generally composed of two small waves, that is, a small wave relating to atrial contraction and a small wave relating to left ventricular pressure rising period (illustration of the small waves are omitted in FIG. 4). The anacrotic limb 31 is a section from the rise of the pulse wave to the peak 32, and exhibits a substantially linear elevation from the rise point in the case of a healthy young person. A latter half crest near the peak 32 is called a tidal wave 33 and is considered to be caused from a reflected wave of an arterial wave. The dicrotic notch 34 is a notch existing between the systole and the diastole of the pulse wave, and is caused from the closing of the aortic valve. The dicrotic wave 35 is a crest appearing at start of the diastole.

Figure 5:
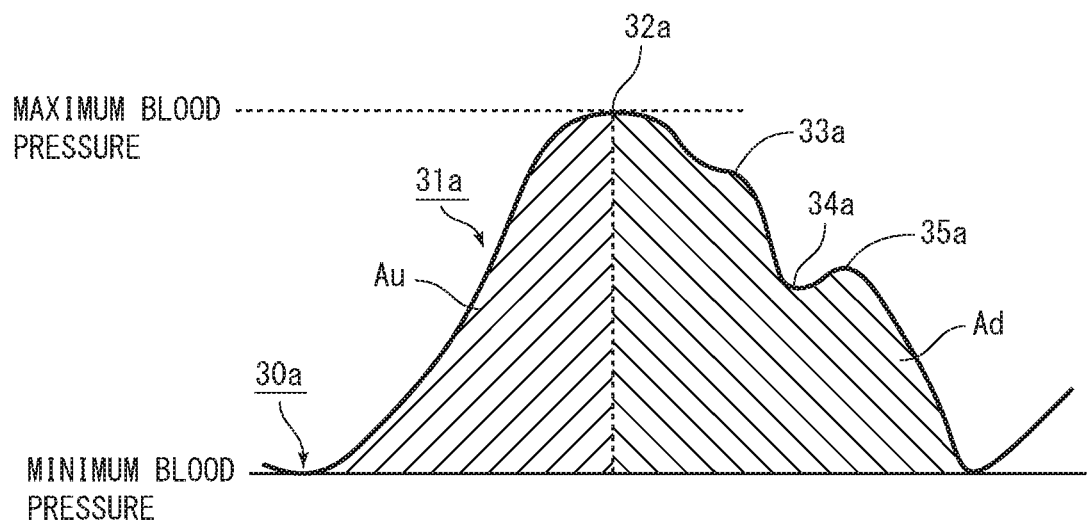
FIG. 5 is a chart illustrating a state of one of the pulse waves illustrated in FIG. 3 taken out, illustrating a state where the vascular elasticity rate is small.

In a soft blood vessel of the healthy young person with a large elasticity rate, as illustrated in FIG. 4, the anacrotic limb 31 steeply rises and a descent section after the peak 32 is gentle. On the other hand, in a hard blood vessel with a small elasticity rate, as illustrated in FIG. 5, an anacrotic limb 31a is gentle. As described above, by investigating the degree of change between the elevation process and the descent process of the pulse wave form, the elasticity rate of the blood vessel can be measured.

Hence, in this embodiment, the degree of hardness of the blood vessel is called a vascular elasticity rate, and is defined by the following expression using a logarithm. More specifically, the control unit 10 as the elasticity rate deriving means uses the logarithm when deriving the vascular elasticity rate.

Vascular elasticity rate=$\text{Log}_e|(\text{maximum blood pressure/minimum blood pressure})/((\text{plus area}-\text{minus area})/(\text{minus area}))|$ The aforementioned plus area and minus area will be described here. As illustrated in FIG. 4 and FIG. 5, the plus area means an area of a region Au being a portion covered by diagonal lines directing from the upper right to the lower left that is a portion of the pulse wave form from the minimum blood pressure to the peak 32, 32a. The minus area means an area of a region Ad being a portion covered by diagonal lines directing from the upper left to the lower right that is a portion of the pulse wave form from the peak 32, 32a to the minimum blood pressure. Hereinafter, the area Au is called a plus area Au and the region Ad is called a minus area Ad.

For example, as an example of the subject having a soft blood vessel of the healthy young person, when the maximum blood pressure is 110 mmHg, the minimum blood pressure is 70 mmHg, the plus area Au is 10 cm², and the minus area Ad is 30 cm², the vascular elasticity rate becomes $\text{Log}_e|(110/70)/(10-30)/30)|=0.85.$ On the other hand, as an example of the subject having a hard blood vessel, when the maximum blood pressure is 110 mmHg, the minimum blood pressure is 70 mmHg, the plus area Au is 20 cm², and the minus area Ad is 25 cm², the vascular elasticity rate becomes $\text{Log}_e|(110/70)/(20-25)/25)|=2.06.$ Alternatively, the vascular elasticity rate can be found by focusing attention on the volume change rate of the blood vessel. According to the Boyle-Charles law, when the temperature is constant, the pressure change and the volume change are in a 1-to-1 relationship. The volume change rate of the blood vessel is a rate indicating how much volume change of the blood vessel occurs in a given time. Hence, for example, assuming that the time period from the time when the pre-ejection wave 30 is recorded to the time when the peak 32 is recorded as t1 time in FIG. 4, when a value obtained by replacing the pressure change from the pre-ejection wave 30 to the peak 32 with the volume change is V1 cm³ (V1 cubic centimeter), the volume change rate in the t1 time becomes V1 cm³/t1 time.

At this time, the control unit 10 as the elasticity rate deriving means replaces a value derived from the volume change rate of the blood vessel being the rate of the volume change of the blood vessel in the t1 time as a predetermined time with a length of one side of a rectangle, replaces a value derived from the t1 time with a length of the other side adjacent to the one side of the rectangle, sets the area of the rectangle obtained by multiplying the length of the one side and the length of the other side as the volume change rate area, calculates a plus volume change rate area in the elevation process of the pulse wave amplitude and a minus volume change rate area in the descent process thereof, and calculates the vascular elasticity rate using values thereof. Note that a square is included as one form of the rectangle as a matter of course.

For example, when the length of the one side of the above-described rectangle in the elevation process of the pulse wave amplitude is set to V1 mm (millimeter) as a value derived from the volume change rate V1 cm³/t1, and the length of the other side adjacent to the one side of the rectangle is set to t1 mm as a value derived from the t1 time, the plus volume change rate area becomes (V1×t1) mm² (square millimeter). This is indicated as a plus volume change rate area Au' in FIG. 6.

Subsequently, when the volume change until a lapse of the t1 time from the time when the peak 32 is recorded is V2 cm³, the volume change rate in the t1 time becomes V2 cm³/t1 time. Thus, when the length of the one side of the above-described rectangle in the descent process of the pulse wave amplitude is set to V2 mm (millimeter) as a value derived from the volume change rate V2 cm³/t1, and the length of the other side adjacent to the one side of the rectangle is set to t1 mm as a value derived from the t1 time, the minus volume change rate area becomes (V2×t1) mm² (square millimeter). This is indicated as a minus volume change rate area Ad' in FIG. 6.

Figure 6:
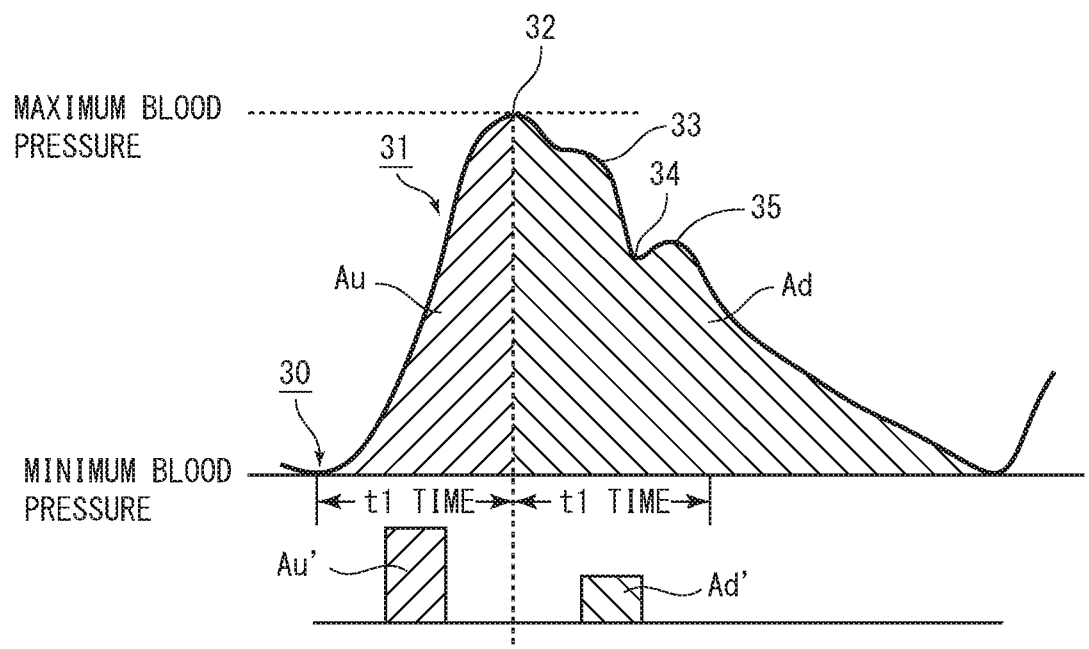
FIG. 6 is a chart illustrating a volume change rate area together with the pulse wave in FIG. 4.
Figure 7:
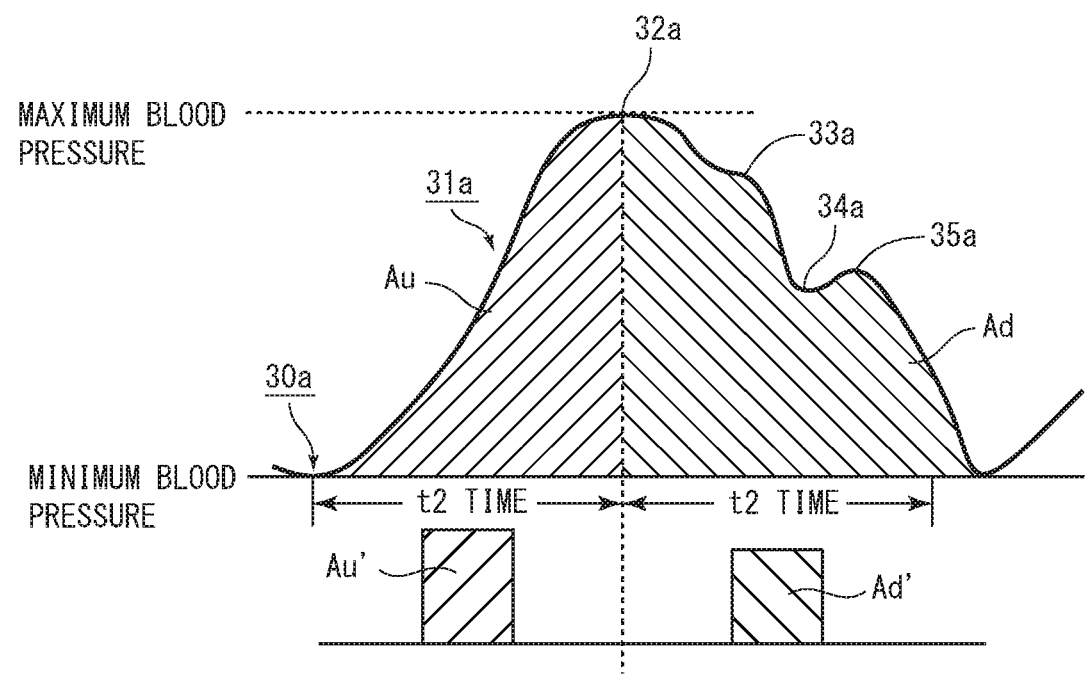
FIG. 7 is a chart illustrating a volume change rate area together with the pulse wave in FIG. 5.

For comparison, in addition to the example of the subject having the soft blood vessel of the healthy young person illustrated in FIG. 6, an example of the subject having the hard blood vessel is illustrated in FIG. 7. In the example in FIG. 7, t2<t2) time has elapsed from a pre-ejection wave 30a to a peak 32a.

Introduction of the concept of the volume change rate area of the blood vessel as described above makes it possible to define the vascular elasticity rate by the following expression.

Vascular elasticity rate=$\text{Log}_e$|(maximum blood pressure/minimum blood pressure)/((plus volume change rate area−minus volume change rate area)/(minus volume change rate area))|

For example, as an example of the subject having the soft blood vessel of the healthy young person, when the maximum blood pressure is 110 mmHg, the minimum blood pressure is 70 mmHg, the plus volume change rate area Au' is 20 cm$^2$, and the minus volume change rate area Ad' is 10 cm$^2$, the vascular elasticity rate becomes $\text{Log}_e$|(110/70)/(20−10)/10)|=0.45.

On the other hand, as an example of the subject having the hard blood vessel, when the maximum blood pressure is 110 mmHg, the minimum blood pressure is 70 mmHg, the plus volume change rate area Au' is 35 cm$^2$, and the minus volume change rate area Ad' is 30 cm$^2$, the vascular elasticity rate becomes $\text{Log}_e$|(110/70)/(35−30)/30)|=2.24.

Introduction of the concept of the volume change rate area of the blood vessel as described above makes the difference between the value indicating the soft blood vessel and the value indicating the hard blood vessel larger than that in the case of not introducing the concept of the volume change rate area of the blood vessel. In short, introduction of the concept of the volume change rate area of the blood vessel makes it possible to acquire information on the vascular elasticity rate with high sensitivity.

Thus, the vascular elasticity rate of the subject can be measured based on the difference in magnitude between the plus area Au and the minus area Ad or between the plus volume change rate area Au' and the minus volume change rate area Ad'. In this case, a smaller value indicates a softer blood vessel. In contrast to this, the degree of change in pulse wave amplitude between the elevation process and the descent process can be derived also from the pressure value in a range where the pulse wave amplitude has been acquired, using a reciprocal. More specifically, the control unit 10 as the elasticity rate deriving means can also set the reciprocal of the derived vascular elasticity rate as the index of the vascular elasticity rate. Thus, by obtaining the reciprocal of the calculated result, a larger numerical value can represent a softer blood vessel. More specifically, in the example of using the above-described plus area Au and minus area Ad, 1/0.85=1.18 (blood vessel is soft), and 1/2.06=0.49 (blood vessel is hard). Besides, in the example of using the above-described plus volume change rate area Au' and minus volume change rate area Ad', 1/0.45=2.22 (blood vessel is soft), and 1/2.24=0.45 (blood vessel is hard).

The vascular elasticity rate can be obtained for each pulsation as described above. For example, as illustrated in FIG. 3, when pulse waves of seven pulsations can be measured in one blood pressure measurement, the vascular elasticity rate can be obtained seven times. In this event, when an error numerical value is calculated due to the influence such as noise by comparing the measured results of the vascular elasticity rate of the seven times as in the smoothing processing at Step S12 in the flowchart in FIG. 2, the noise can be found and removed. For example, if the measured results of five times among the measured results of the seven times fall within a range indicating that the blood vessel is soft, whereas the measured results of two times fall within a range indicating that the blood vessel is hard, the measured results of the two times can be determined as error.

Further, as illustrated at Step S13 in the flowchart in FIG. 2, how many times a correct numerical value has been recorded in seven times can be displayed as an "accuracy index". For example, between the case where the correct numerical value has been recorded four times out of seven times and the case where the correct numerical value has been recorded five times out of seven times, the measured results of the latter case can be determined to be higher in accuracy than the measured results of the former case.

Figure 8:
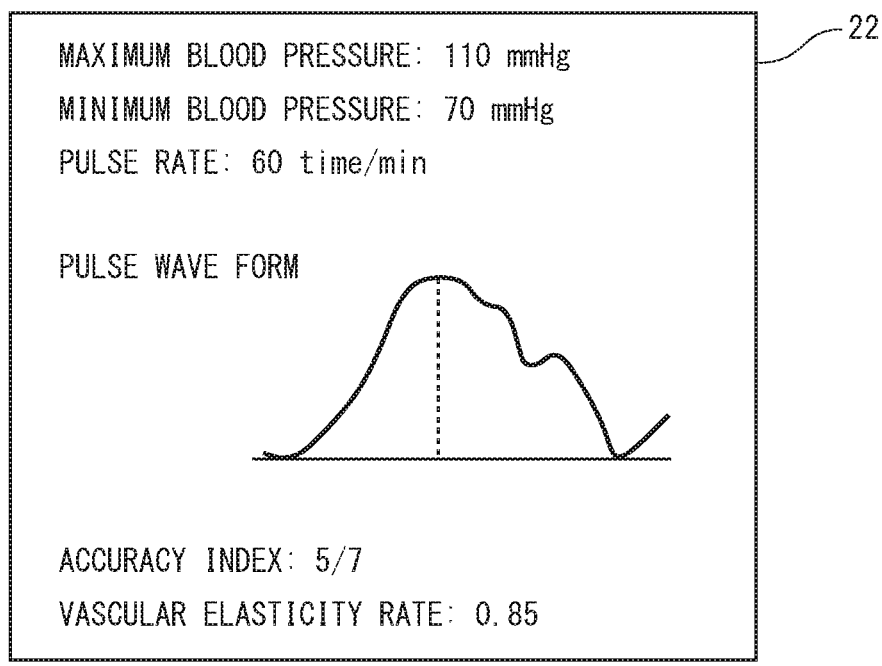
FIG. 8 is a chart illustrating a display example of a display device in FIG. 1.

FIG. 8 illustrates a display example of the display device 22. The display device 22 displays the maximum blood pressure, the minimum blood pressure, the pulse rate, the pulse wave form, the accuracy index, and the vascular elasticity rate. Note that an accuracy index (5/7) illustrated in FIG. 8 means that the correct numerical value has been obtained in five pulsations out of seven pulsations of the pulse wave.

Note that for keeping the same measurement accuracy by using the hemodynamics evaluation apparatus in PTL 2, the blood pressure measurement needs to be performed seven times. Thus, the hemodynamics evaluation apparatus in PTL 2 requires a time period seven times that of the vascular elasticity rate evaluation apparatus 1 according to this embodiment.

As described above, according to the vascular elasticity rate evaluation apparatus 1, the measurement of the vascular elasticity rate with high accuracy can be performed in a short time.

Figure 9:
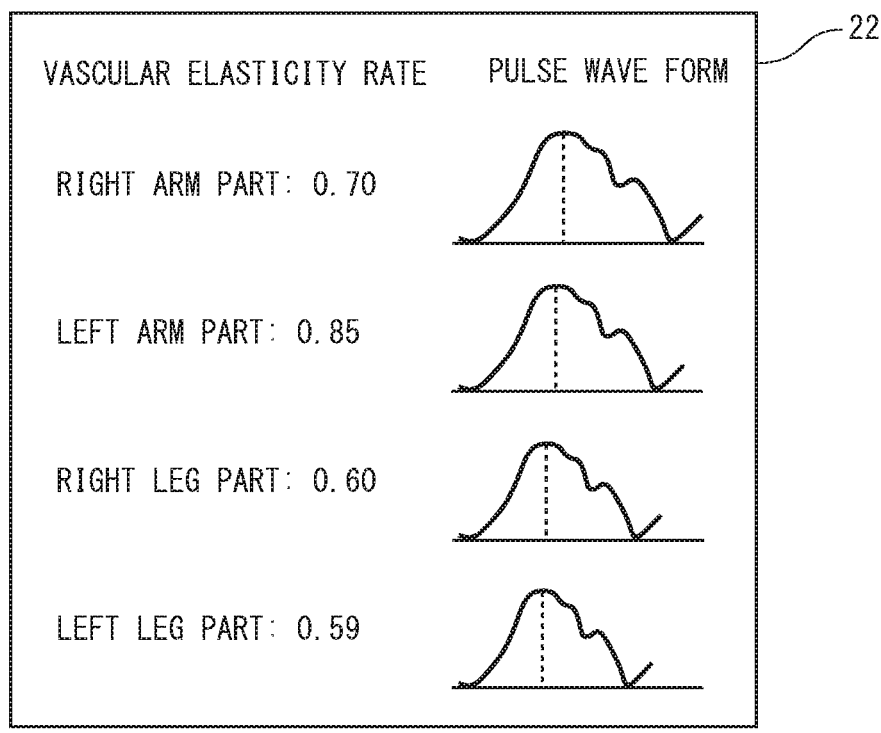
FIG. 9 is a chart illustrating a display example of the display device in FIG. 1, individually indicating measured results at a plurality of different places.

Further, the vascular elasticity rate evaluation apparatus 1 can measure the vascular elasticity rate at each portion of the subject around which the cuff 18 is wound. This enables the display device 22 to individually display the vascular elasticity rates measured at a plurality of portions (the right arm part, the left arm part, the right leg part, and the left leg part in the example in FIG. 9) of the subject as illustrated in FIG. 9.

Note that the blood pressure/pulse wave inspection apparatus in PTL 3 detects the whole pulse waves of the subject by winding a plurality of cuffs around a plurality of portions including the upper arm and the lower leg of the subject. In this case, it is impossible to detect the pulse wave at each portion of the subject and also impossible to measure the vascular elasticity rate at each portion of the subject. In contrast to this, the vascular elasticity rate evaluation apparatus 1 according to this embodiment can detect the pulse wave at each portion of the subject, and therefore can measure and display the vascular elasticity rate at each portion of the subject. As described above, measurement and display of the vascular elasticity rate at each portion of the subject is very important in specifying local problems of the blood vessel of the subject.

Other embodiments

The above-described embodiment can be variously modified without departing from its gist. For example, a plurality of cuffs 18 and pressure detection units 26 as the pulse wave detection means may be provided. This enables the control unit 10 as the elasticity rate deriving means to sequentially or simultaneously measure the vascular elasticity rates at a plurality of portions of the subject, by winding the cuffs 18 around the plurality of portions of the subject. Thus, the vascular elasticity rates at the plurality of portions of the subject can be measured without being affected by temporal change of the condition of the subject.

Besides, the measurement of the vascular elasticity rate has been mainly described in the above embodiment, and the pumping property of a heart can be additionally measured.

Besides, the above-described mathematical expressions are examples, and any mathematical expressions may be used as long as they can derive the degree of elasticity of the blood vessel. For example, as an example using no logarithm, Vascular elasticity rate=|((maximum blood pressure−minimum blood pressure)/((plus area−minus area)/(minus area))|×100 may be used. Alternatively, as the mathematical expression for finding an elastic index EI of the blood vessel as another index of the vascular elasticity rate, when a height from the minimum blood pressure to the peak 32 illustrated in FIG. 4 is a (millimeter) and a height from the minimum blood pressure to the tidal wave 33 is b (millimeter), $EI=a/b$ may be used. Furthermore, RI (renal vascular resistance) may be associated with these mathematical expressions.

Furthermore, by using the vascular elasticity rate in the following expression, a local index of the pulse wave velocity can also be calculated.

Pulse wave velocity local index=√((vascular elasticity rate×diastolic blood pressure)/(2×blood density))

REFERENCE SIGNS LIST

10 . . . control unit (means for forming a pulse wave amplitude, elasticity rate deriving means), 11 . . . pressure detector (part of pulse wave detection means), 12 . . . pressure detection circuit (part of pulse wave detection means), 13 . . . CPU (part of means for forming a pulse wave amplitude, part of elasticity rate deriving means), 16 . . . constant-rate exhaust means (constant-rate exhaust unit), 17 . . . pressure means (pressure unit), 18 . . . cuff (part of pulse wave detection means), 19 . . . buffer memory (part of means for forming a pulse wave amplitude, part of elasticity rate deriving means), 20 . . . storage memory (part of means for forming a pulse wave amplitude, part of elasticity rate deriving means), 21 . . . external operation unit, 22 . . . display device (means for displaying), 23 . . . printing device, 24 . . . input/output terminal, 26 . . . pressure detection unit (part of pulse wave detection means)

The invention claimed is:

1. A vascular elasticity rate evaluation apparatus comprising:
a pulse wave detection means for detecting a pulse wave with an external pressure being applied to a blood vessel;
a means for forming a pulse wave amplitude from a detection value of the pulse wave detection means; and
an elasticity rate deriving means for deriving a vascular elasticity rate using measured values in processes for an elevation process and a descent process of the pulse wave amplitude,
wherein
the elasticity rate deriving means is configured to derive the vascular elasticity rate as follows:

Vascular elasticity rate=Log$_e$|(maximum blood pressure/minimum blood pressure)/((plus area−minus area)/(minus area))|, and wherein the plus area means an area of a region of the pulse wave from the minimum blood pressure to a peak, and the minus area means an area of a region of the pulse wave from the peak to the minimum blood pressure.

2. The vascular elasticity rate evaluation apparatus according to claim 1, further comprising:
a means for individually displaying vascular elasticity rates measured at a plurality of portions of a subject.

3. The vascular elasticity rate evaluation apparatus according to claim 1, further comprising:
a plurality of the pulse wave detection means,
wherein the elasticity rate deriving means sequentially or simultaneously measures the vascular elasticity rates at a plurality of portions of a subject.

* * * * *